US009014410B2

(12) United States Patent
Matsuo et al.

(10) Patent No.: US 9,014,410 B2
(45) Date of Patent: Apr. 21, 2015

(54) EARPHONE DEVICE

(71) Applicant: Sony Corporation, Tokyo (JP)

(72) Inventors: Tomohiro Matsuo, Saitama-Ken (JP); Takashi Ohta, Tokyo (JP); Koji Nageno, Tokyo (JP); Tomohiro Ito, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/899,076

(22) Filed: May 21, 2013

(65) Prior Publication Data

US 2013/0251186 A1 Sep. 26, 2013

Related U.S. Application Data

(63) Continuation of application No. 11/651,557, filed on Jan. 10, 2007, now Pat. No. 8,611,581.

(30) Foreign Application Priority Data

Jan. 12, 2006 (JP) ................................ 2006-005412

(51) Int. Cl.

| | |
|---|---|
| ***H04R 25/00*** | (2006.01) |
| ***H04R 1/10*** | (2006.01) |
| ***H04R 1/34*** | (2006.01) |
| *A61B 7/02* | (2006.01) |
| *H04R 29/00* | (2006.01) |

(52) U.S. Cl.

CPC ............ *H04R 1/1066* (2013.01); *H04R 1/1016* (2013.01); *H04R 1/345* (2013.01); *H04R 29/001* (2013.01); *H04R 1/10* (2013.01); *H04R 1/1091* (2013.01)

(58) Field of Classification Search

USPC ........... 381/380–384, 370, 371, 376; 181/135
See application file for complete search history.

(56) References Cited

U.S. PATENT DOCUMENTS

| | | | | |
|---|---|---|---|---|
| 2,136,720 A * | 11/1938 | White | ........................... | 381/151 |
| 2,188,591 A * | 1/1940 | Carlson | ......................... | 381/380 |
| 2,430,229 A | 11/1947 | Kelsey | | |
| 4,972,492 A | 11/1990 | Tanaka et al. | | |
| 5,784,471 A | 7/1998 | Bebenroth | | |
| 5,949,896 A | 9/1999 | Nageno et al. | | |
| 6,292,565 B1 | 9/2001 | Chamberlin et al. | | |

(Continued)

FOREIGN PATENT DOCUMENTS

| | | |
|---|---|---|
| DE | 101 11 636 A1 | 9/2002 |
| EP | 0 825 796 A2 | 2/1998 |

(Continued)

OTHER PUBLICATIONS

Japanese Office Action dispatched May 14, 2013, in Japanese Patent Application No. 2013-023154, with English translation (10 pages).

(Continued)

*Primary Examiner* — Curtis Kuntz
*Assistant Examiner* — Sunita Joshi
(74) *Attorney, Agent, or Firm* — Finnegan, Henderson, Farabow, Garrett & Dunner, L.L.P.

(57) ABSTRACT

An earphone device includes a housing having a driver unit, and a sound guide tube mounted on a front surface of the housing to protrude from the front surface, in which the sound guide tube is disposed at a position deviated from a center position of the housing.

20 Claims, 16 Drawing Sheets

(56) References Cited

U.S. PATENT DOCUMENTS

| | | | | |
|---|---|---|---|---|
| 6,683,965 | B1 | 1/2004 | Sapiejewski | |
| 6,738,487 | B1 | 5/2004 | Nageno et al. | |
| 7,079,664 | B2 | 7/2006 | Nassimi | |
| 7,155,134 | B2 | 12/2006 | Azadet | |
| 7,212,646 | B2 | 5/2007 | Nassimi | |
| 7,349,550 | B2 * | 3/2008 | Oliveira et al. | 381/380 |
| 7,372,974 | B2 | 5/2008 | Yanagishita et al. | |
| 7,616,772 | B2 | 11/2009 | Sabick et al. | |
| 2003/0059071 | A1 | 3/2003 | Dunham | |
| 2005/0147269 | A1 | 7/2005 | Oliveira et al. | |
| 2006/0098836 | A1 | 5/2006 | Sabick et al. | |
| 2007/0189570 | A1 | 8/2007 | Matsuo et al. | |

FOREIGN PATENT DOCUMENTS

| | | | |
|---|---|---|---|
| EP | 1 058 479 | A2 | 12/2000 |
| JP | 40-27928 | A | 9/1965 |
| JP | 57-026987 | A | 2/1982 |
| JP | 58-043700 | A | 3/1983 |
| JP | 01-117598 | | 5/1989 |
| JP | HEI 01-117598 | | 5/1989 |
| JP | HEI 01-137691 | | 9/1989 |
| JP | U 1-137691 | A | 9/1989 |
| JP | 4-107992 | U | 9/1992 |
| JP | 6-59120 | | 8/1994 |
| JP | 6-81351 | | 10/1994 |
| JP | HEI 07-115695 | | 5/1995 |
| JP | 07-154888 | A | 6/1995 |
| JP | 07154888 | A * | 6/1995 |
| JP | 07-322383 | A | 12/1995 |
| JP | HEI 08-172691 | | 7/1996 |
| JP | HEI 09-9363 | | 1/1997 |
| JP | 973861 | | 2/1997 |
| JP | 09-065476 | A | 3/1997 |
| JP | 09-307983 | A | 11/1997 |
| JP | HEI 09-307983 | | 11/1997 |
| JP | 10-066181 | A | 3/1998 |
| JP | 2000-308172 | A | 11/2000 |
| JP | 2000-341784 | A | 12/2000 |
| JP | 2003-32772 | | 1/2003 |
| JP | 2003-032772 | A | 1/2003 |
| JP | 2003-125476 | | 4/2003 |
| JP | 2005-191663 | | 7/2005 |
| JP | 2007-189468 | A | 7/2007 |
| WO | WO 2005/069677 | A1 | 7/2005 |
| WO | WO 2007/031340 | A2 | 3/2007 |

OTHER PUBLICATIONS

Japanese Office Action dispatched May 14, 2013, in Japanese Patent Application No. 2013-079086, with English translation (6 pages).
Communication from the Japanese Patent Office dated Nov. 6, 2008, for Japanese Patent Application No. 2006-005412.
Communication from Japanese Patent Office dated Mar. 31, 2011, for Japanese Patent Application No. 2009-053594.
Communication from the Chinese Patent Office dated Apr. 20, 2011, for Chinese Patent Application No. 200710001705.5.
European Examination Report dated Jun. 9, 2009, issued in corresponding European Patent Application No. 07100467.5.
European Examination Report dated Aug. 12, 2010, issued in corresponding European Patent Application No. 07100467.5.
European Extended Search Report dated May 9, 2007, issued in corresponding European Patent Application No. 07100467.5.
Office Action issued in U.S. Appl. No. 11/651,557 mailed on Nov. 23, 2010.
Office Action issued in U.S. Appl. No. 11/651,557 mailed on Dec. 27, 2011.
Office Action issued in Japanese Patent Application No. 2009-053594 mailed on Dec. 18, 2012.
Product Brochure for My Ear II and Pro Ear.
Notification of Reason for Refusal issued in Japanese Patent Application No. 2013-079085, dated Aug. 6, 2013, with English translation.
Japanese Office Action mailed on Apr. 1, 2014, issued for Japanese Application No. 2013-135957, and English translation, 7 pages.
Comunication mailed by the Japan Patent Office on Nov. 25, 2014 for Japanese Application No. 2013-135957, and English language translation thereof, 4 pages.
Communication mailed by the Japan Patent Office on Nov. 25, 2014 for Japanese Application No. 2013-135957, and English language translation thereof, 5 pages.
Communication mailed by the Japan Patent Office on Dec. 16, 2014 for Japanese Application No. 2014-093856, and English language translation thereof, 14 pages.
Japanese Office action mailed on Sep. 9, 2014, issued for Japanese Application No. 2013-135957, and English translation, 4 pages.

* cited by examiner

FIG. 11

| No. | NAME | DIFFERENCE BETWEEN MEASUREMENT EARPHONE AND OPTIMUM ANGLE IN FITTING STATE (° ) |
|---|---|---|
| 1 | OSHIMA | 3 |
| 2 | SUZUKI | 25 |
| ⋮ | ⋮ | ⋮ |
| 32 | TAGAWA | 0 |
| 33 | SONE | 10 |

Prior Art

EARPHONE DEVICE

CROSS REFERENCES TO RELATED APPLICATIONS

This application is a continuation of U.S. patent application Ser. No. 11/651,557, filed Jan. 10, 2007, which claims priority to Japanese Patent Application No. 2006-005412, filed Jan. 12, 2006, the entire disclosures of which are incorporated herein by reference.

BACKGROUND OF THE INVENTION

1. Field of the Invention

The present invention relates to earphone devices. For example, the present invention may be applied to an earplug type earphone device in which a sound tube is inserted to an external auditory meatus with an earpiece interposed therebetween.

2. Description of the Related Art

An earphone device typically vibrates a diaphragm disposed in a driver unit accommodated in a housing (a casing of the earphone device) in accordance with audio signals supplied from a portable music player or the like, varies a compression state of air, and thus generates sound corresponding to the audio signals.

For example, according to a lateral in-the-ear earphone device, a housing of the earphone device is supported by a tragus and an antitragus of a user, so that the earphone device fits in an ear of the user (for example, see Japanese Examined Patent Application Publication No. 6-81351).

In the above earphone device, since the shape of a pinna varies from person to person, a gap may be present between the housing and an external auditory meatus when the user wears the earphone device, resulting in leakage of sound through the gap.

In addition, in the above earphone device, since the shapes of the tragus and the antitragus vary from person to person, the user may not support the housing by the tragus and the antitragus, resulting in deterioration in fitting comfortability such as that fitting state is not maintained for a long time.

Meanwhile, according to a vertical in-the-ear earphone device, a diaphragm is arranged to directly oppose the entrance of the external auditory meatus of the user, and hence, the shape around the entrance of the external auditory meatus less influences the sound. Accordingly, such an earphone device may provide stable, high-quality sound to the user (for example, see Japanese Examined Patent Application Publication No. 6-59120).

In the above earphone device, a holder, such as a band or a hanger, is used for holding the earphone device when the user wears the earphone device, resulting in lack of portability. Also, the band is located over the top of the head thereby making the user's hair untidy.

To address the disadvantages with the lateral in-the-ear and the vertical in-the-ear earphone devices, as shown in FIGS. 15A to 150, there is provided an earplug type earphone device 30 which, includes an earpiece 31 having a profile corresponding to the external, auditory meatus when the user wears the earphone device 30, a substantially cylindrical sound guide tube 32 provided in the earpiece 31, a substantially spherical housing 33 in which the sound guide tube 32 is mounted, a cord retainer 34 integrally provided with the housing 33, and a cord 7 connected to a driver unit (not shown) provided in the housing 33.

FIG. 15A is a lateral elevational view showing the earphone device 30 in the Y-Z plane. FIG. 15B is a rear elevational view showing the earphone device 30 in the X-Z plane. FIG. 150 is a bottom plan view showing the earphone device 30 in the X-Y plane.

The housing 33 vibrates a diaphragm disposed in the driver unit in accordance with audio signals supplied through the cord 7, and thus generates sound corresponding to the audio signals.

The sound guide tube 32 protrudes from the center portion of a front surface of the housing 33, and when the user wears the earphone device 30, the sound guide tube 32 is inserted to the external auditory meatus with the earpiece 31 interposed therebetween, so that the sound output via the driver unit of the housing 33 is guided to the external auditory meatus.

The earpiece 31 is formed of flexible material so that its shape is freely deformable. Once the earpiece 31 is inserted to the external auditory meatus, the earpiece 31 is closely attached to the external auditory meatus, thereby maintaining the fitting state in which the earpiece 31 is closely attached to the user's ear, and providing gentle fitting.

SUMMARY OF THE INVENTION

In the above earphone device 30, as shown in FIG. 16A which is a cross section of the user who wears the earphone device 30 viewed from the top taken along the line XVI-XVI, since the width W2 of the housing 33 is restricted to prevent the housing 33 from abutting on a tragus 22, the size of a diaphragm (not shown) accommodated in the housing 33 is also restricted. Accordingly, the diaphragm is relatively small.

Due to this, the earphone device 30 only secures a small amount of air at the front of the diaphragm to be compressed or decompressed to output bass sound, and in addition, the air generally flows to the sides of the diaphragm. Accordingly, a compression state of air may not vary sufficiently, and hence, the bass sound may not be output effectively.

In addition, as shown in FIG. 16B which is a cross section of the user who wears an earphone device 35 viewed from the top taken along the line XVI-XVI, in a case of the earphone device 35 that employs a housing 36 having a width W3 slightly larger than the width W2 of the housing 33, a diaphragm accommodated in the housing 36 may increase in size by the increment of the width W3 of the housing 36. However, when the earphone device 35 fits in the user's ear, the housing 36 may abuts on the tragus 22, and hence, it is difficult to maintain the fitting state, and even to insert the earphone device 35 to the ear.

With the earplug type earphone device 30, the size of the diaphragm tends to be restricted for improving the fitting state, resulting in difficulty of providing sufficiently high-quality sound. Contrary, fitting comfortability may be deteriorated if the diaphragm increases in size.

To address the above-described disadvantages, it is desirable to provide an earphone device which provides comfortable fitting, and high-quality sound.

An earphone device according to an embodiment of the present invention includes a housing having a driver unit, and a sound guide tube mounted on a front surface of the housing to protrude from the front surface, in which the sound guide tube is disposed at a position deviated from a center position of the housing.

With this configuration, when the user wears the earphone device in the ear, the width of the housing may be large as compared with the related art without the housing abutting on the tragus. Owing to this, an aperture of a diaphragm disposed in a driver unit accommodated in the housing may increase in size, and thereby providing high-quality sound with improved fitting comfortability for the user. Therefore, there may be provided the earphone device which provides comfortable fitting, and high-quality sound.

BRIEF DESCRIPTION OF THE DRAWINGS

FIG. 11 is a table showing measurement results.

DESCRIPTION OF THE PREFERRED EMBODIMENTS

An embodiment of the present invention will be described below with reference to the attached drawings.

1. External Configuration of Earphone Device

Figure 1:
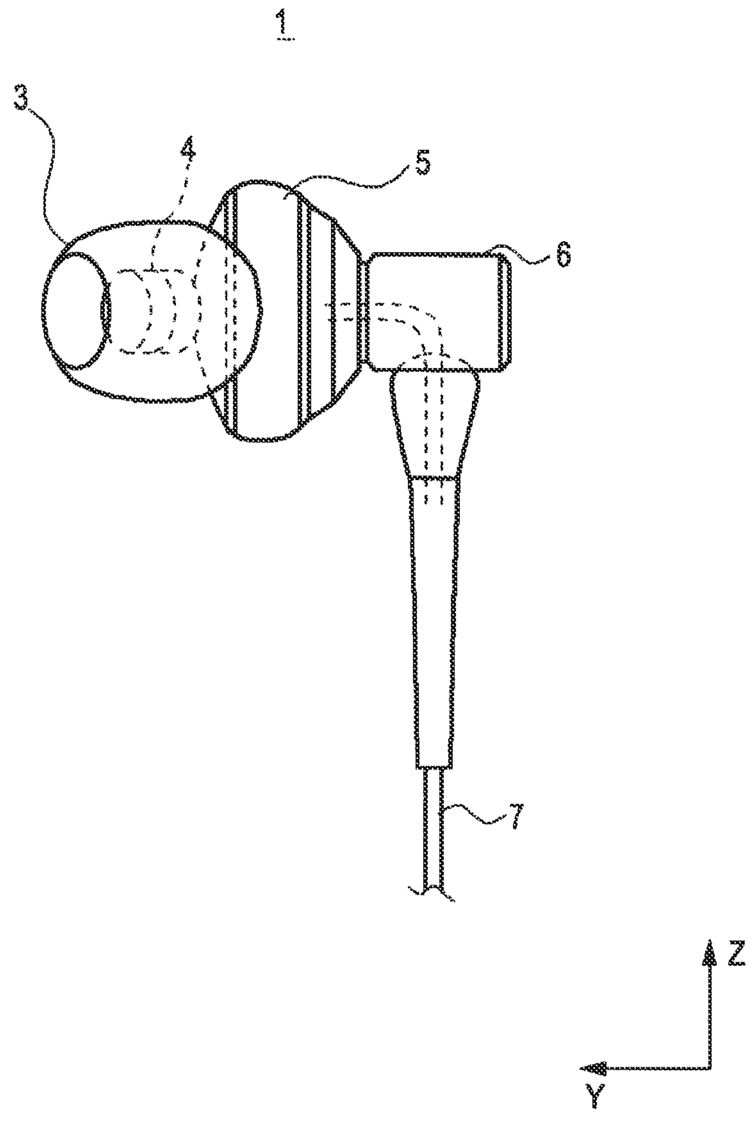
FIG. 1 is a lateral elevational view showing an earphone device according to an embodiment of the present invention.
Figure 2:
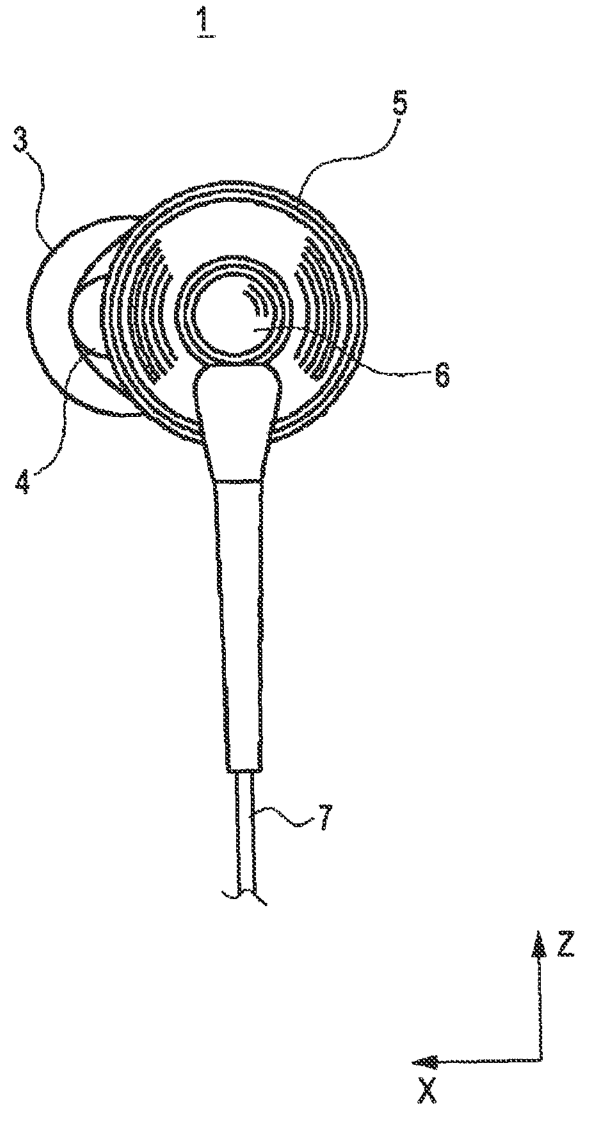
FIG. 2 is a rear elevational view showing the earphone device according to the embodiment of the present invention.
Figure 3:
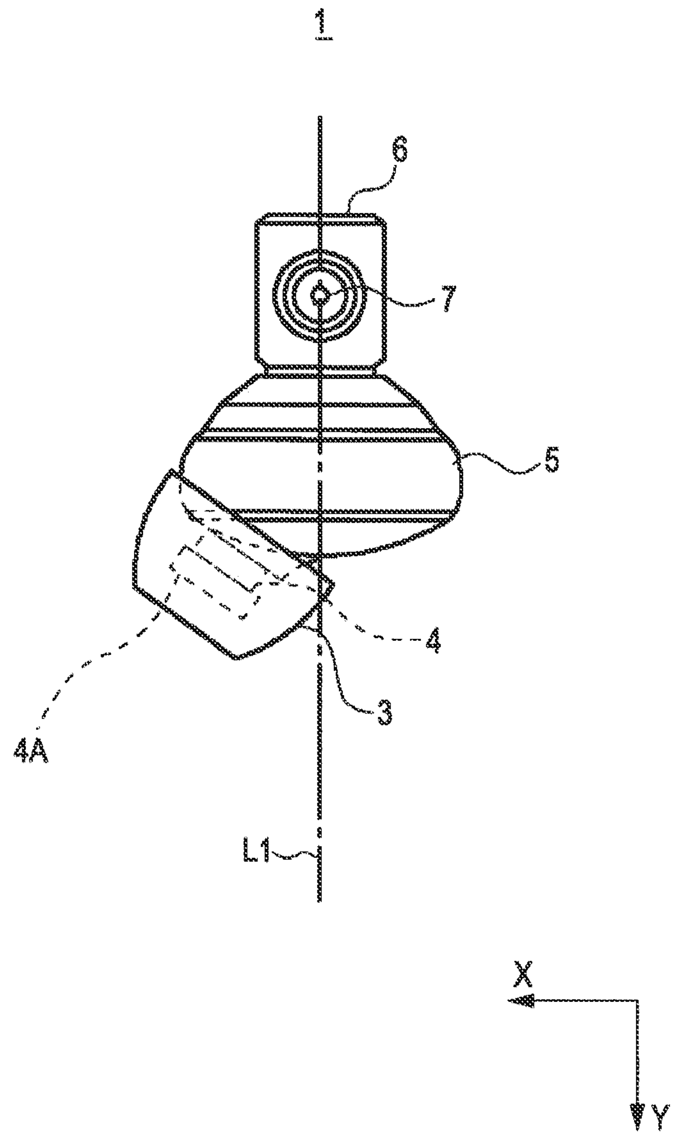
FIG. 3 is a bottom plan view showing the earphone device according to the embodiment of the present invention.

In FIGS. 1 to 3, an earphone device 1 according to an embodiment of the present invention is shown. The earphone device 1 includes an earpiece 3 having a shape corresponding to an external auditory meatus of a user in a fitting state, a substantially cylindrical sound guide tube 4 provided in the earpiece 3, a substantially spherical housing 5 in which the sound guide tube 4 is mounted, a substantially cylindrical cord retainer 6 integrally provided with the housing 5, and a cord 7 connected to a driver unit disposed in the housing 5.

FIG. 1 is a lateral elevational view showing the earphone device in the Y-Z plane. FIG. 2 is a rear elevational view showing the earphone device 1 in the X-Z plane. FIG. 3 is a bottom plan view showing the earphone device 1 in the X-Y plane.

As shown in FIG. 1, the earphone device 1 vibrates a diaphragm (not shown) disposed in the driver unit (not shown) accommodated in the housing 5 in accordance with audio signals supplied from a portable music player or the like (not shown) through the cord 7 connected to the player, varies a compression state of air present at, the front of the diaphragm, and thus may generate sound corresponding to the audio signals.

The cord retainer 6 of the earphone device 1 fixes a drawn position of the cord 7 being drawn from the housing 5, and allows the user to pinch the cord retainer 6 with finger tips when the user wears the earphone device 1.

Figure 16A:
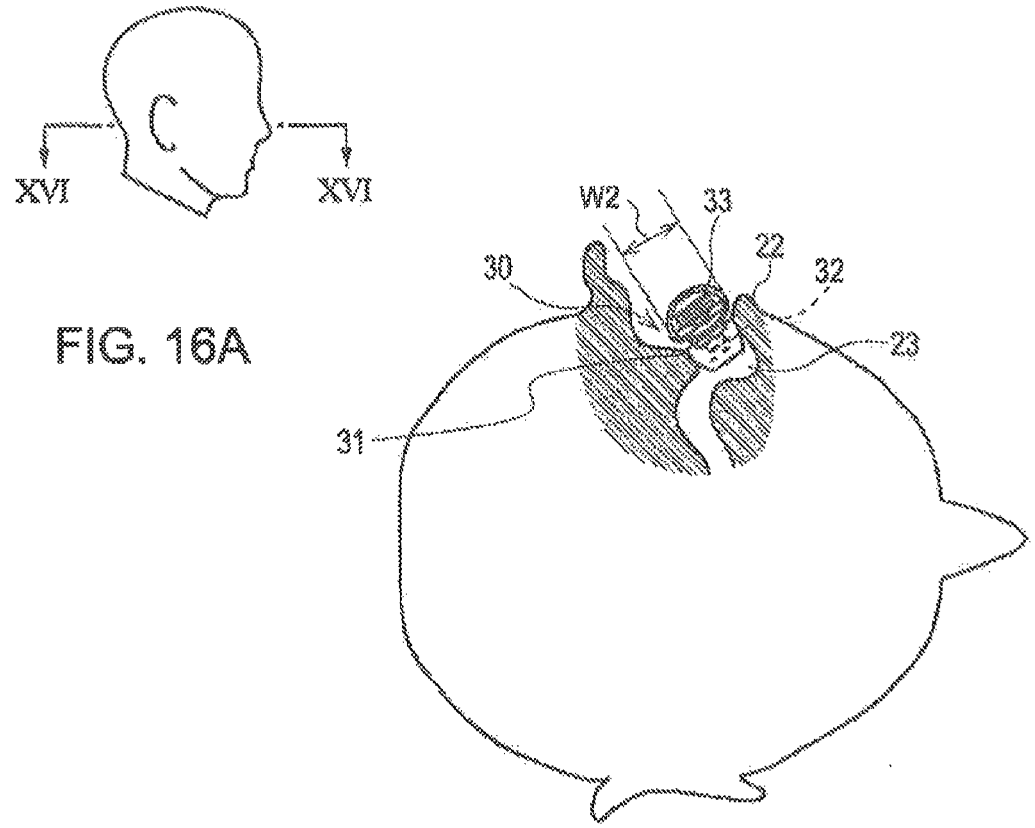
FIGS. 16A and 16B are cross sections viewed from the top each showing the earphone device of the related art in the fitting state.
Figure 16B:
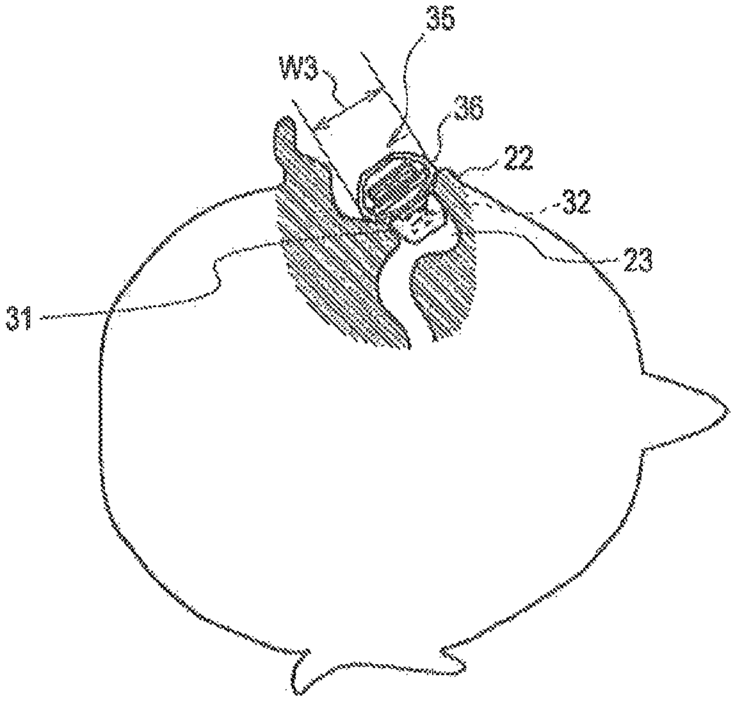
FIG. 16B Prior Art

As shown in FIGS. 1 and 3, the cylindrical sound guide tube 4 integrated to and protrudes from a front surface of the housing 5, so that sound is guided to an external auditory meatus 23 (FIG. 16) from a sound guide tube tip 4A in the fitting state of the earphone device 1.

The sound guide tube 4 uses ABS (Acrylonitril Butadiene Styrene) resin as its material. Accordingly, the sound output from the housing 5 may be guided to the external auditory meatus 23 while substantially no sound leaks outside.

The earpiece 3 uses silicon rubber as its material, thus having flexibility. In the fitting state of the earphone device 1, the earpiece 3 may deform corresponding to a profile of the external auditory meatus 23 and may be closely attached thereto, so that substantially no sound, which is guided from the sound guide tube 4, leaks outside.

2. Internal Configuration of Earphone Device

Next, the internal configuration of the earphone device 1 will be described below with reference to FIGS. 4 to 6 in which the same numerals are applied to the components corresponding to those in FIG. 1.

Figure 4:
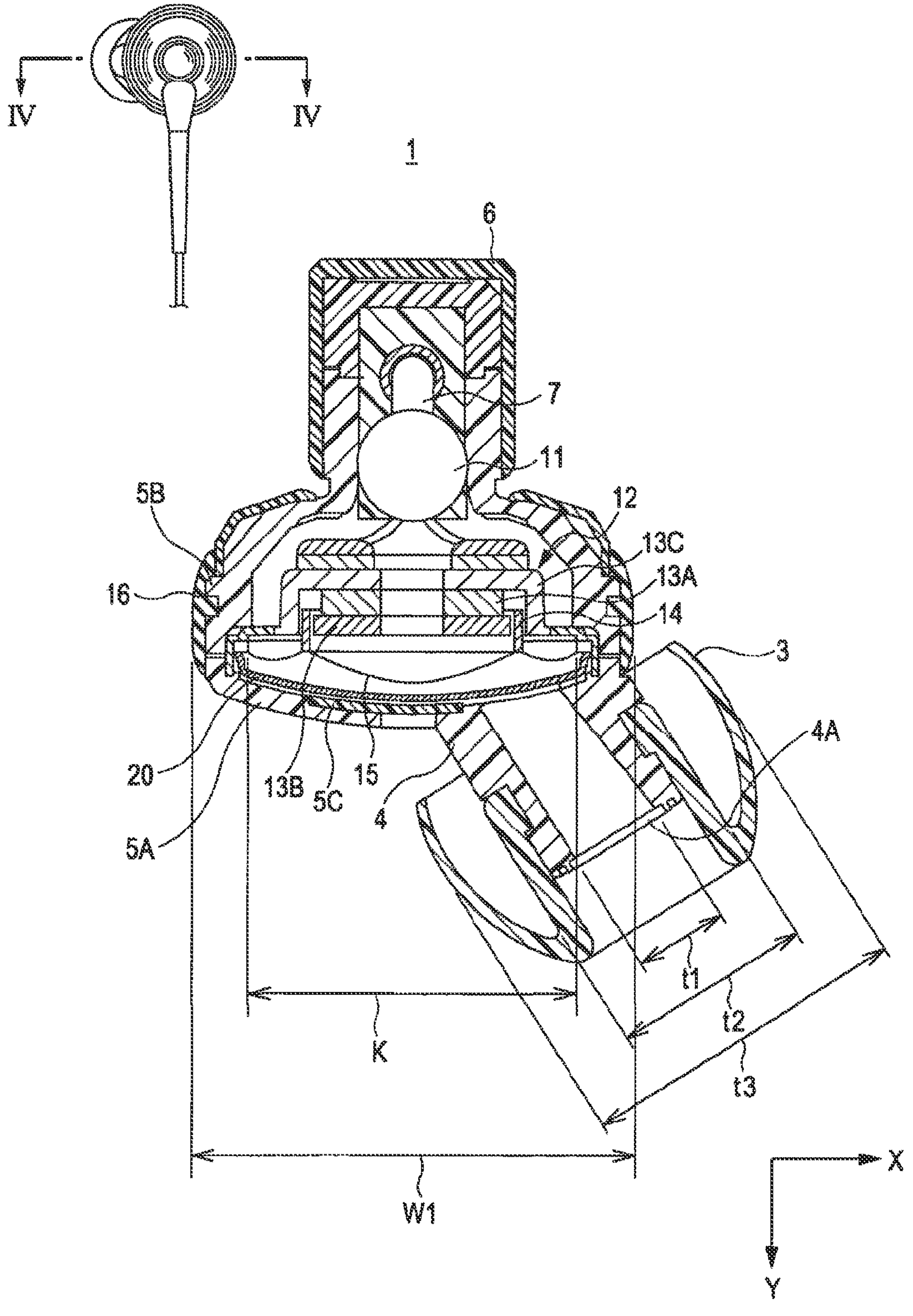
FIG. 4 is a cross section viewed from the top showing a left earphone unit of the earphone device according to the embodiment of the present invention.

FIG. 4 is a cross section viewed from the top showing the earphone device 1 taken along the line IV-IV. FIG. 5 is a cross section viewed from the lateral side showing the earphone device 1 taken along the line VV. FIG. 6 is a cross section viewed from the rear side showing the earphone device 1 taken along the line VI-VI.

Figure 5:
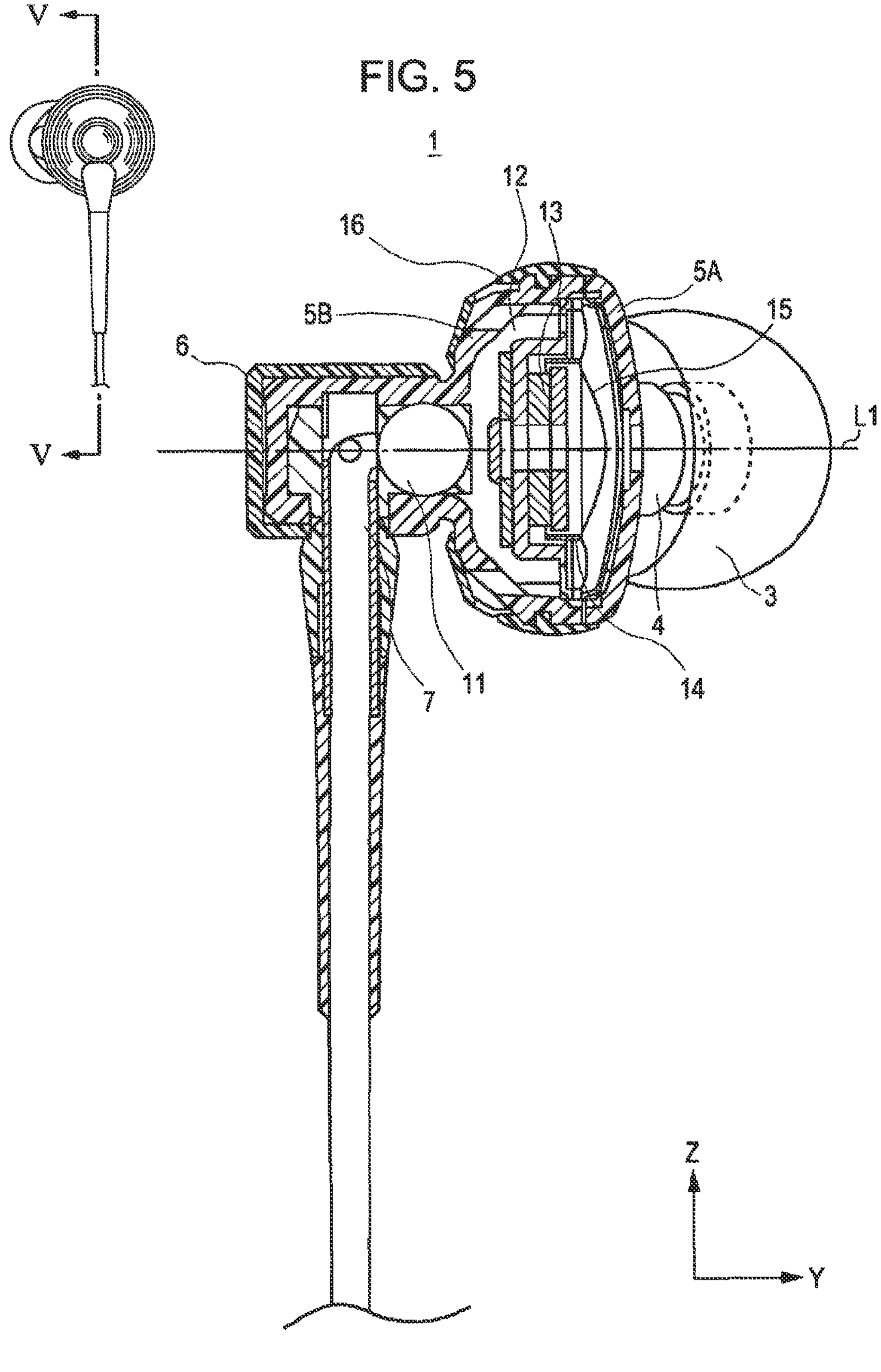
FIG. 5 is a cross section viewed from the lateral side showing the left earphone unit of the earphone device according to the embodiment of the present invention.

As shown in FIGS. 4 and 5, the housing 5 includes a housing front portion 5A and a housing rear portion 5B made of plastic and connected to each other by ultrasonic welding to reliably keep the inner space of the housing 5 airtight.

When the housing front portion 5A and the housing rear portion 5B are connected to each other by ultrasonic welding, resin which melts at the welding may leak outside. To protect and conceal such resin, the housing 5 is sealed with an annular rubber 16.

The housing 5 has a width W1 which is larger than the width W2 (FIG. 16A) of the housing 33 of the related art. Accordingly, a diaphragm 15 larger than the diaphragm (not shown) of the housing 33 of the related art may be accommodated in the housing 5.

Figure 6:
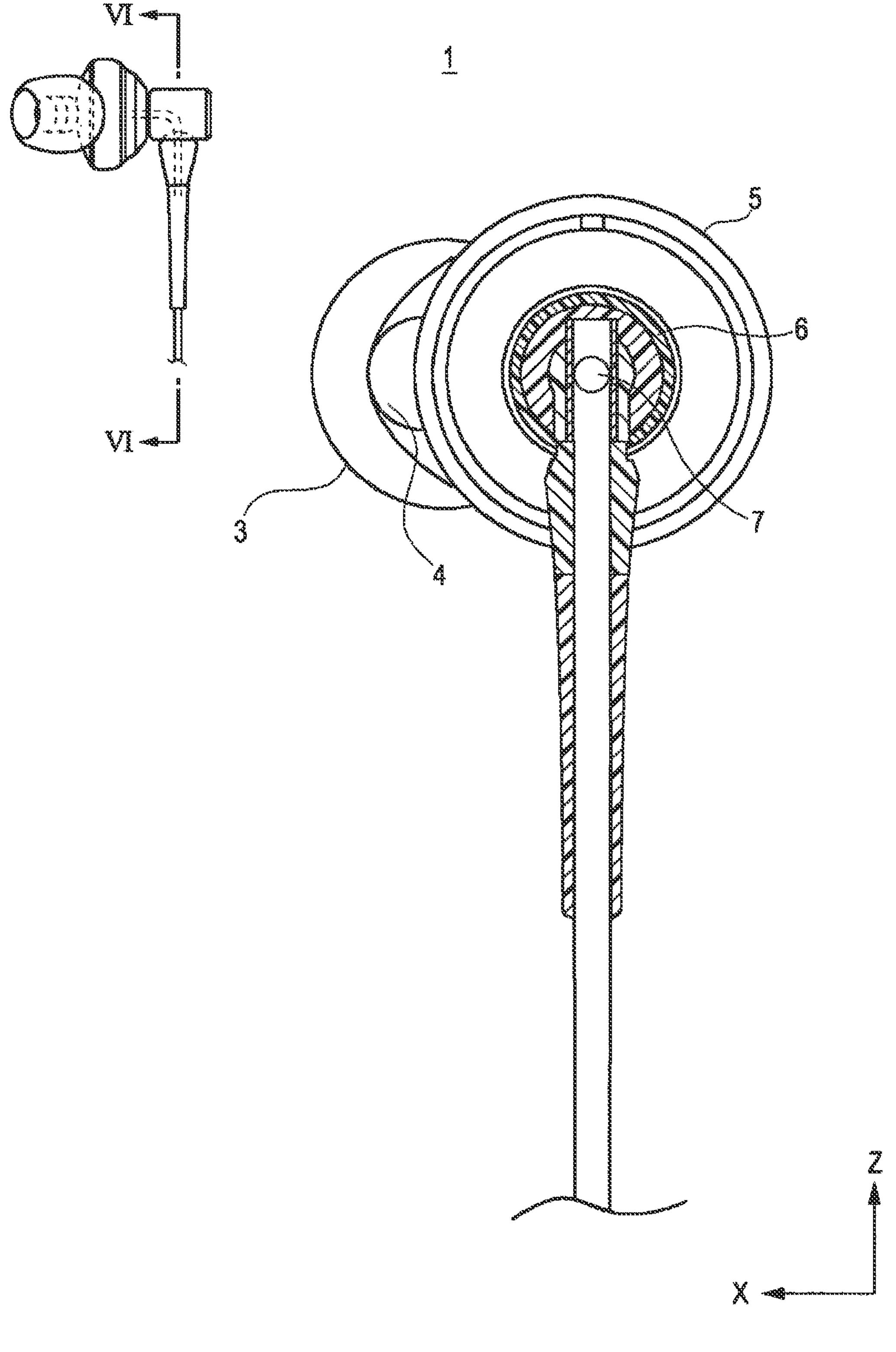
FIG. 6 is a cross section viewed from the rear side showing the left earphone unit of the earphone device according to the embodiment of the present invention.

As shown in FIGS. 5 and 6, the cord retainer 6 accommodates a cord knot 11 of the cord 7 to function as a stopper that prevents the cord 7 from slipping out of the housing 5 when the cord 7 is pulled.

As shown in FIGS. 4 and 5, a driver unit 12 accommodated in the housing rear portion 5B of the housing 5 includes a magnetic circuit having a magnet 13A, a plate 13B and a yoke 13C; a voice coil 14 inserted to a magnetic gap defined between the plate 13B and the yoke 13C; a disk-like diaphragm 15 attached to the voice coil 11; and a porous, metallic circular protection plate 20 spaced from the diaphragm 15 by a certain distance. The housing front portion 5A is disposed at a front circular opening of the housing rear portion 5B opposing the protection plate 20, with a cushion member 5C made from a rubber plate or the like interposed therebetween. The housing front portion 5A presses the driver unit 12 toward the housing rear portion 58 flexibly with the cushion member 5C, and hence, the housing 5 may accommodate the driver unit 12 without rattling. The diaphragm 15 is driven in accordance with the audio signals input, to the voice coil 14 through the cord 7, the compression state of air present at the front of the diaphragm 15 varies, and the sound corresponding to the audio signals is guided outside through the sound guide tube 4.

3. Offset and Angle Determination Method of Sound Guide Tube

Figure 15A:
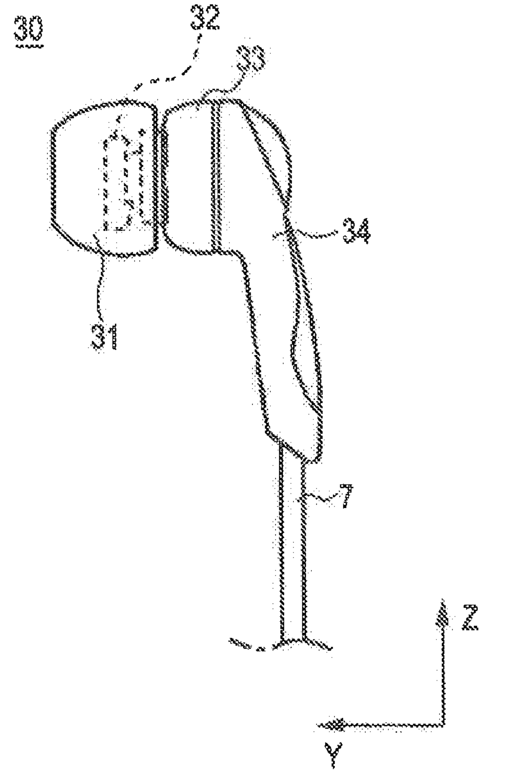
FIGS. 15A to 15C are schematic illustrations each showing a structure of an earphone device of a related art.
Figure 15B:
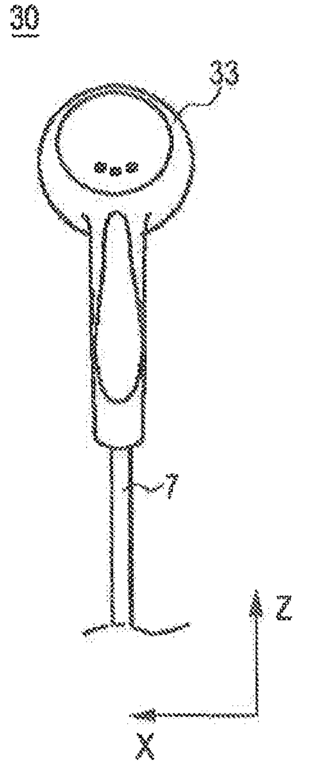
Figure 15C:
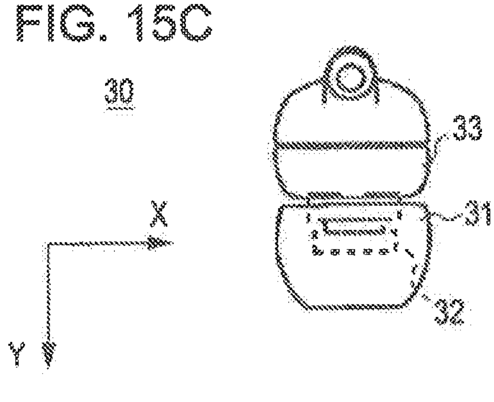

When the earphone device 1 (FIG. 3) is compared with the earphone device 30 (FIG. 15C) of the related art, the sound guide tube 4 protruding from the front surface of the housing 5 is attached to be deviated in the X-axis direction from a center line of the driver unit 12, i.e., a center line L1 of the housing 5. Namely, the sound guide tube 4 is offset in the X-axis direction by a predetermined offset amount with reference to the center line L1 of the housing 5.

In addition, when the earphone device 1 is compared with the earphone device 30 of the related art, the sound guide tube tip 4A is directed in a direction away from the centerline L1 of the housing 5. Namely, the sound guide tube 4 tilts relative to the Y-axis by a predetermined angle (hereinafter, referred to as a tilt angle).

Figure 7:
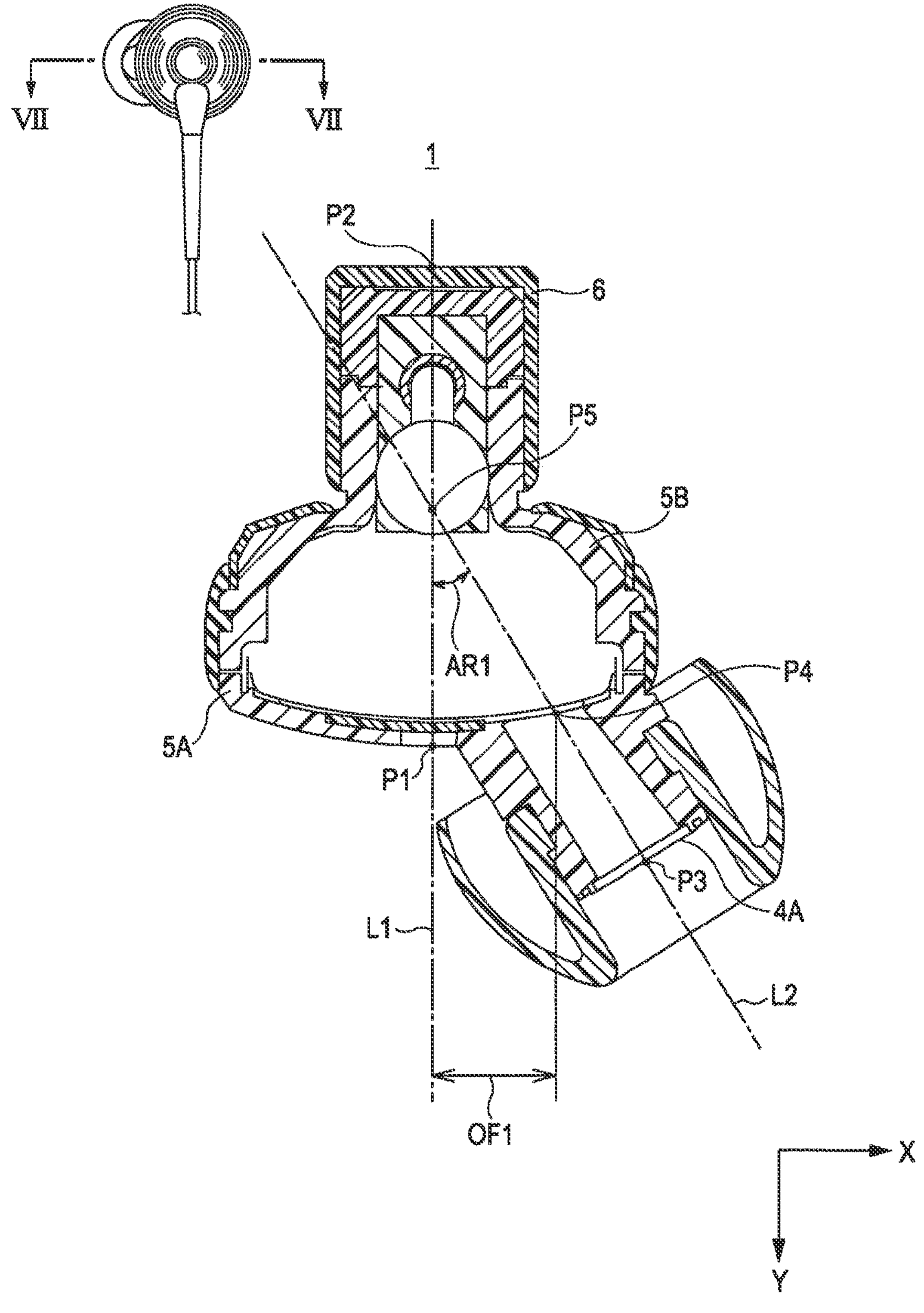
FIG. 7 is a schematic illustration used for description of offset and tilt of the earphone device.

The offset amount and the tilt angle of the sound guide tube 4 will be described with reference to FIG. 7 which is a cross section viewed from the top showing the earphone device 1 taken along the line VII-VII.

The center line L1 of the housing 5 is plotted by connecting a center point of the front surface of the housing front portion 5A (hereinafter, referred to as a housing front portion midpoint P1) and a center point of the rear surface of the cord retainer 6 (hereinafter, referred to as a cord retainer midpoint P2). A center axis line L2 of the sound guide tube 4 is plotted by passing through a center point of the sound guide tube tip 4A (hereinafter, referred to as a sound guide tube tip midpoint P3). An intersection point P5 is determined by the center axis line L2 of the sound guide tube 4 and the center line L1 of the housing 5. Hence, a tilt, angle AR1 is defined about the intersection point P5 as a tilt of the sound guide tube 4 with respect to the housing 5. An intersection point is determined by the center axis line L2 of the sound guide tube 4 and the housing front portion 5A (hereinafter, referred to as a sound guide tube base point P4). Hence, an offset amount OF1 is given by a distance from the center line L1 to the base point P4 in the X-axis direction in the X-Y plane.

3-1. Offset Determination Method of Sound Guide Tube

With this offset determination method, the offset amount OF1 is determined by measurement using a dummy ear produced by making a mold of an ear of an actual person. In this embodiment, the offset amount OF1 is determined as 5 mm for instance.

3-2. Tilt Angle Determination Method of Sound Guide Tube

Next, a procedure for determining an angle for the tilt angle AR1 of the sound guide tube 4 with respect to the front surface of the housing 5, will be described.

Figure 8:
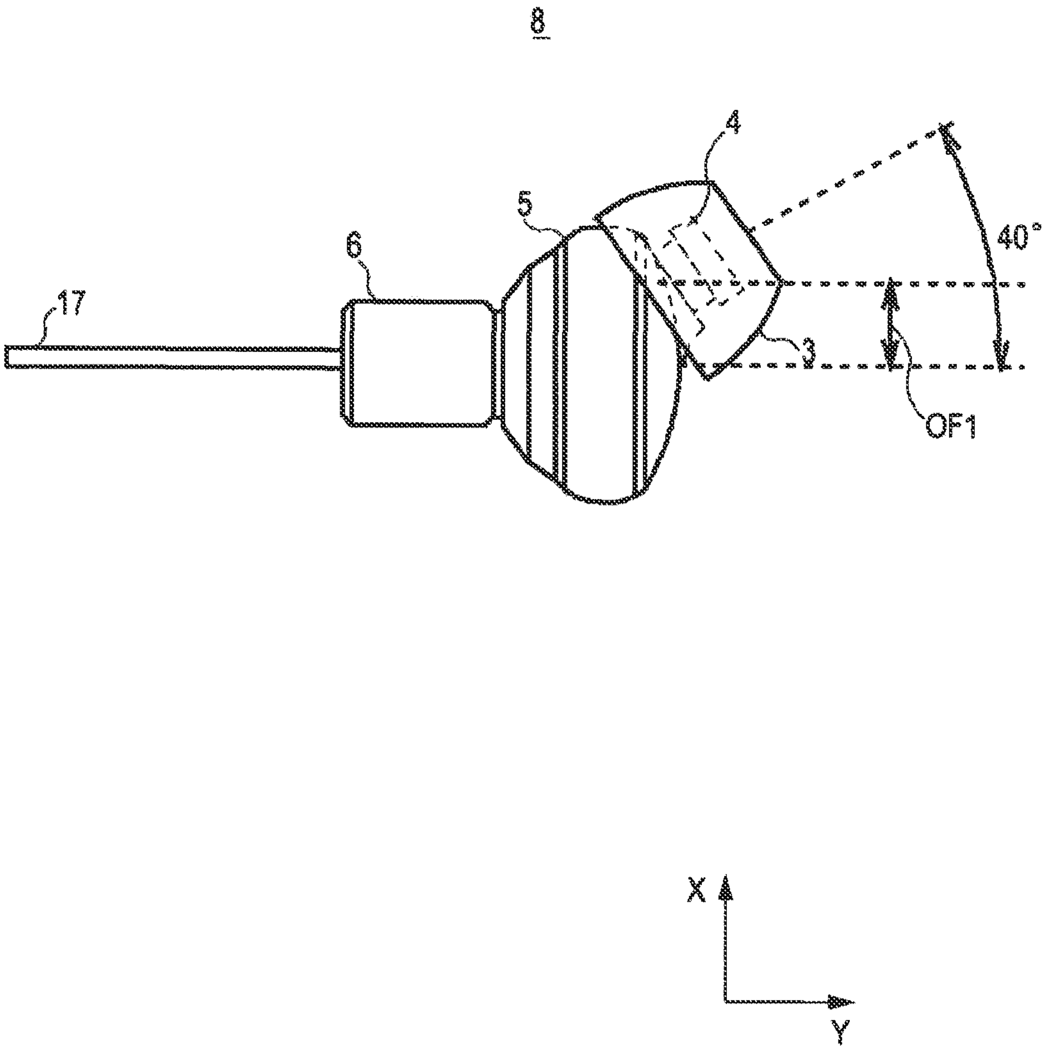
FIG. 8 is a top plan view showing a measurement earphone device.

In this tilt angle determination method, as shown in FIG. 8, a measurement earphone device 8 is prepared. The measurement earphone device 8 has a metering rod 17 bonded to the rear surface of the cord retainer 6. For example, the offset amount OF1 of the measurement earphone device 8 is determined as 5 mm, and the tilt angle of the sound guide tube 4 with respect to the front surface of the housing 5 is determined as 40'.

Figure 9:
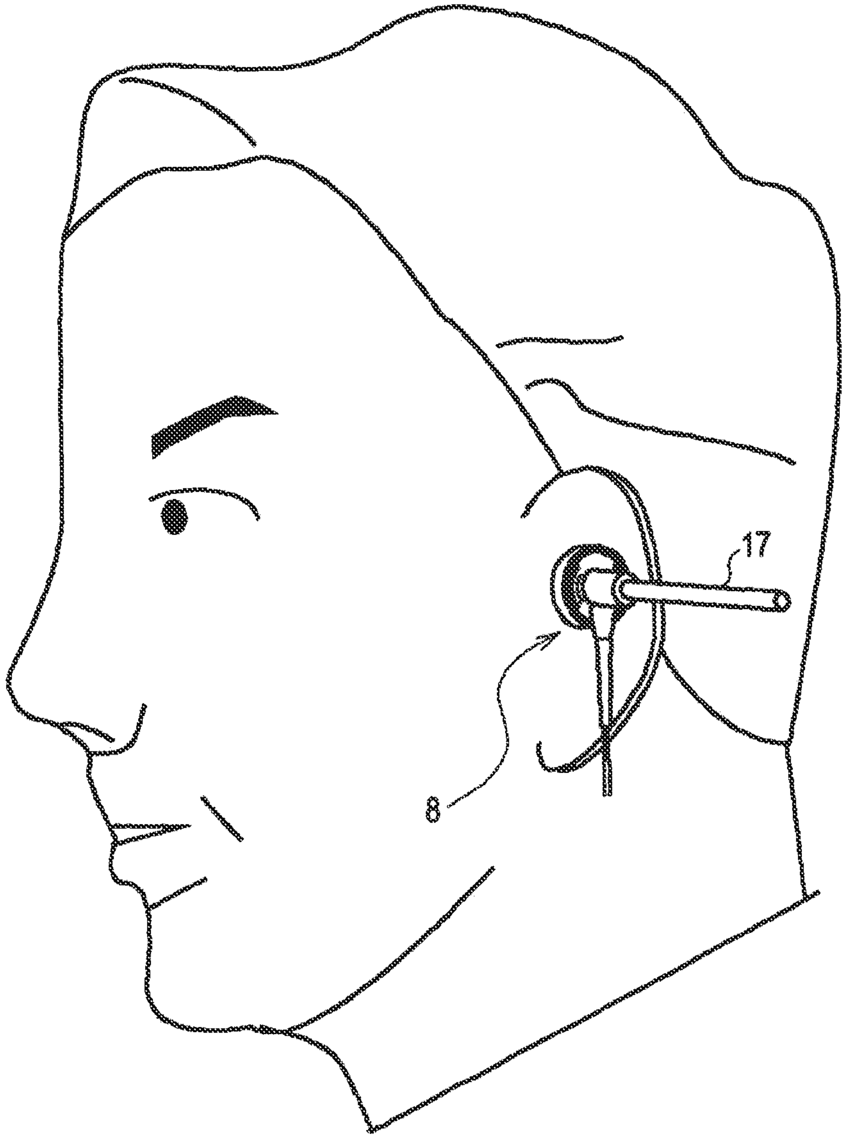
FIG. 9 is a lateral elevational view showing the measurement earphone device in a fitting state.
Figure 10:
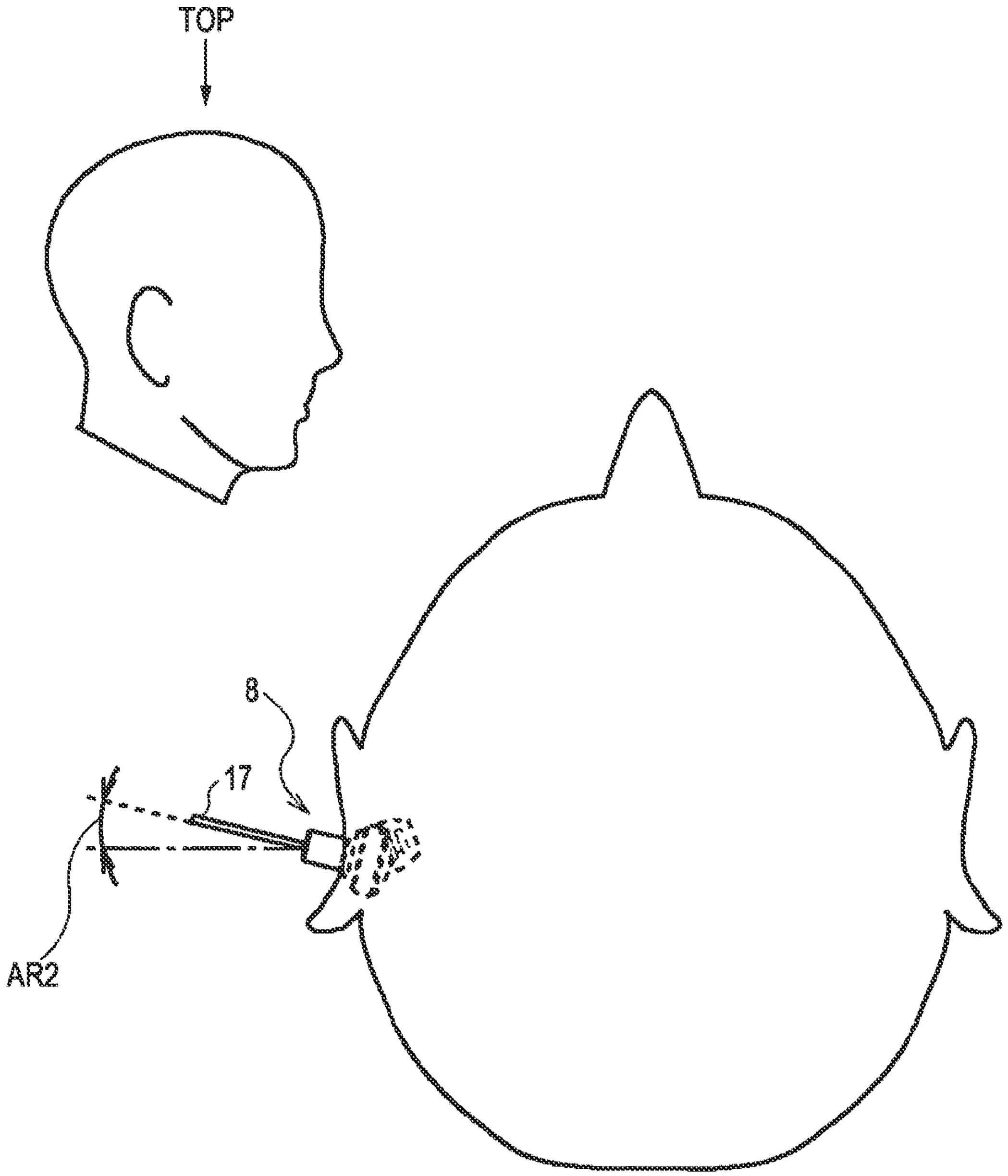
FIG. 10 is a top plan view showing the measurement earphone device in the fitting state.

Then, in this tilt angle determination method, subject persons are randomly selected for measurement, each person wears the measurement earphone device 8 as shown in FIG. 9, and tilt angles AR2 of the metering rod 17 with respect to a lateral surface of a head of each person in an fitting state of the measurement earphone device 8 as shown in FIG. 10.

Further, in the tilt angle determination method, measurement results of the tilt angles AR2 are aggregated, a mean value of the tilt angle AR2 is obtained, and the tilt angle AR1 of the sound guide tube 4 is obtained by subtracting the mean value of the tilt angles AR2 from 40° which is the tilt angle of the sound guide tube 4 of the measurement earphone device 8 with respect to the front surface of the housing 5.

In this tilt angle determination method, the above-described measurement of the tilt angle AR2 is applied to each of the randomly selected 33 subject persons, the measurement results are put into a table shown in FIG. 11, and the mean value of the tilt, angles AR2 is obtained. The mean value of the tilt angles AR2 becomes 7°, the mean value 7° of the tilt angles AR2 is subtracted from the tilt angle 40° of the measurement earphone device 8, and the tilt angle AR1 of the sound guide tube 4 is determined as 33°.

In this embodiment, the above-described measurement of the tilt angle AR2 has been applied to each of the 33 persons.

Therefore, the earphone device 1 may provide comfortable fitting for a user having an ear with a normal shape, by determining the position and the tilt angle of the protrusion of the sound guide tube 4 with respect to the housing 5 according to the above-mentioned offset determination method and the tilt angle determination method, even when the width W1 of the housing 5 is larger than the width W2 of the housing 33 of the related art.

4. Fitting of Earphone Device

Figure 12:
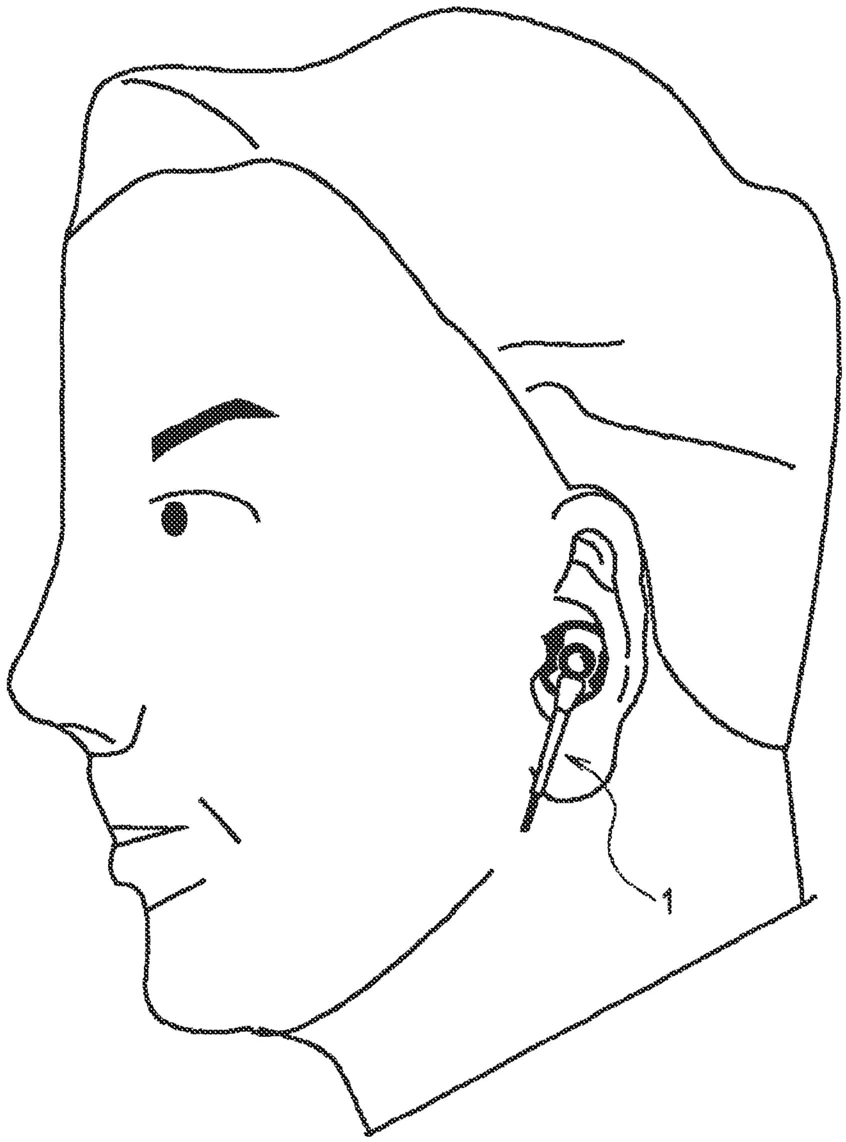
FIG. 12 is a lateral elevational view showing the earphone device in the fitting state.
Figure 13:
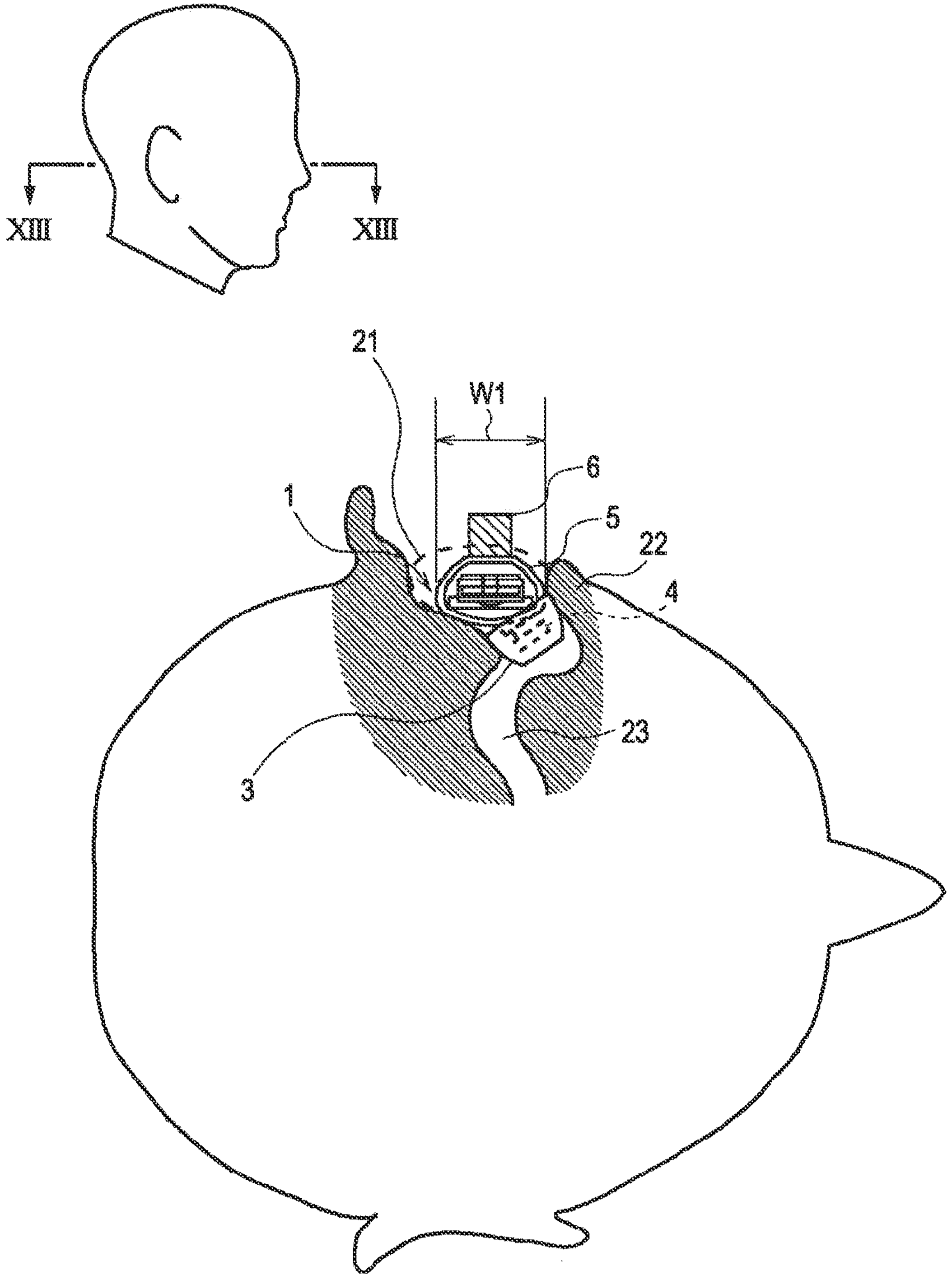
FIG. 13 is a cross section viewed from the top showing the earphone device in the fitting state.

The earphone device 1 fits in the user's ear when the earpiece 3 is inserted to the external auditory meatus 23. FIG. 12 shows the earphone device 1 in the fitting state. FIG. 13 is a cross section viewed from the top showing the earphone device 1 taken along the line XIII-XIII in the fitting state.

As shown in FIG. 13, in the fitting state of the earphone device 1, the housing 5 is located in a cavum conchae 21 indicated by a bold dotted line, and the earpiece 3 deforms corresponding to the shape of the external auditory meatus 23 when the flexible earpiece 3 is inserted to the external auditory meatus 23. Accordingly, the earphone device 1 may be attached closely to the external auditory meatus 23 and maintain the fitting state for a long time.

In the earphone device 1, the width W1 of the housing 5 is larger than the width W2 of the housing 33 of the earphone device 30 (FIG. 16A) of the related art. Accordingly, the diaphragm 15 (FIG. 4) provided in the driver unit accommodated in the housing 5 may also increase in size as compared with the related art. In particular, the diaphragm 15 of the earphone device 1 may have an aperture K (FIG. 4) of 13.5 mm while the earphone device 30 of the related art has an aperture of 9 mm. Accordingly, in a case where 1 kHz sound is output with 1 mW power, it has been proved that the sensitivity of the earphone device 1 may increase by 6 to 8 dB as compared with that of the earphone device 30 of the related art.

In this case, the sound guide tube 4 has an inside diameter t1 of 3.6 mm and an outside diameter t2 of 6.3 mm, the earpiece 3 has an outside diameter t3 of 12 mm, and the housing 5 has a width W1 of 15.5 mm.

5. Action and Effect

With the above-described configuration, in the earphone device 1, the sound guide tube 4 (FIG. 7) is offset in the X-axis direction by the offset amount OF1 with reference to the center line L1 of the housing 5, and the sound guide tube tip midpoint P3 is directed in the direction away from the center line L1. Accordingly, even when the earphone device 1 employs the housing 5 having the width W1 which is larger than the width W2 of the housing 33 of the earphone device 30 of the related art, the user may wear the earphone device 1 without the housing 5 abutting on the tragus 22 (FIG. 13) of the user.

In addition, in the earphone device 1, the offset amount OF1 and the tilt angle AR1 are determined on the basis of the mean value of the actual measurement results. Accordingly, when the user having the ear of the normal shape wears the earphone device 1, the housing 5 would not abut on the tragus 22, and hence it may be prevented that the user may not wear the earphone device 1 or the user feels difficulty for wearing it, thereby providing comfortable fitting.

In addition, in the earphone device 1, the housing 5 has the width W1 (FIG. 13) which is larger than the width W2 (FIG. 16A) of the housing 33 of the earphone device 30 of the related art. Accordingly, the diaphragm 15 (FIG. 4) accommodated in the housing 5 may increase in size, so that the earphone device 1 may provide high-quality sound with effective bass sound as compared with the earphone device 30 of the related art.

In addition, in the earphone device 1, the sound guide tube 4 is offset from the housing 5, and tilts by the tilt angle AR1. Accordingly, even when the housing 5 and the diaphragm 15 increase in size, the earpiece 3 may cc closely attached to the external auditory meatus 23 (FIG. 13) to maintain the fitting state, the earphone device 1 may provide comfortable fitting for the user and high-qua sound.

In addition, the earphone device 1 does not have a band over the top of the head or a hanger over the top of the ear. Accordingly, the earphone device 1 improves usability by addressing the disadvantages such as making the user's hair untidy, or not being portable, due to the provision of the band over the head of the user as disclosed in Japanese Examined Patent. Application Publication No, 6-59120.

With the above-described configuration, the earphone device 1 may provide comfortable fitting and further high-quality sound.

6. Modifications

While the earpiece 3 employs as its material silicon rubber in the above-described embodiment, the present invention is not limited thereto. For example, the earpiece 3 may use a material such as urethane resin or acrylic resin.

While the sound guide tube 4 employs as its material ABS resin in the above-described embodiment, the present invention is not limited thereto. For example, the sound guide tube 4 may use a resin such as polypropylene or polystyrene.

While the sound guide tube 4 employs as its material ABS resin solely in the above-described embodiment, the present invention is not limited thereto. For example, the sound guide tube 4 may use elastomer resin for its base portion, and flexible material such as ABS resin for the residual portions other than the base portion, namely, a material of the sound guide tube 4 may be prepared by coinjection molding.

In such a case, since the sound guide tube 4 is flexible at the portions other than the base portion, the sound guide tube tip 4A may be bent. Accordingly, when the earphone device 1 fits in the user's ear, the sound guide tube 4 and the earpiece 3 may be bent toward a proper direction so that the user feels more comfortable in fitting.

While the diaphragm 15 has the aperture K (FIG. 4) of 13.5 mm in the above-described embodiment, the present invention is not limited thereto. For example, the aperture K may be 13.6 mm, 13.4 mm, and the like, as long as the housing 5 may be located within the cavum conchae 21 (FIG. 13). In such a case, the earphone device 1 may provide the improved fitting comfortability and high-quality sound for the user similarly to the case where the diaphragm 15 has the aperture K of 13.5 mm.

While the tilt angle AR1 of the sound guide tube 4 is determined as 33° in the above-described embodiment, the present invention is not limited thereto. For example, the tilt angle AR1 may be any in a range from 10° to 60°, the range being derived from the number of subject persons and the measurement results. However, majority of the subject persons feel comfortable when wearing the earphone device 1 when the tilt angle AR1 falls within a range from 30° to 50°.

While the offset amount OF1 is determined as 5 mm in the above-described embodiment, the present invention is not limited thereto. Even when the earphone device 1 is applied to various people, including a young woman having a small ear, a man, such as an American or European person, having relatively big ear, and the like, without limiting to the above-described 33 subject persons, majority of people feel comfortable with an offset amount OF1 in a range from 3 to 7 mm when wearing the earphone device 1 for a long time.

Figure 14:
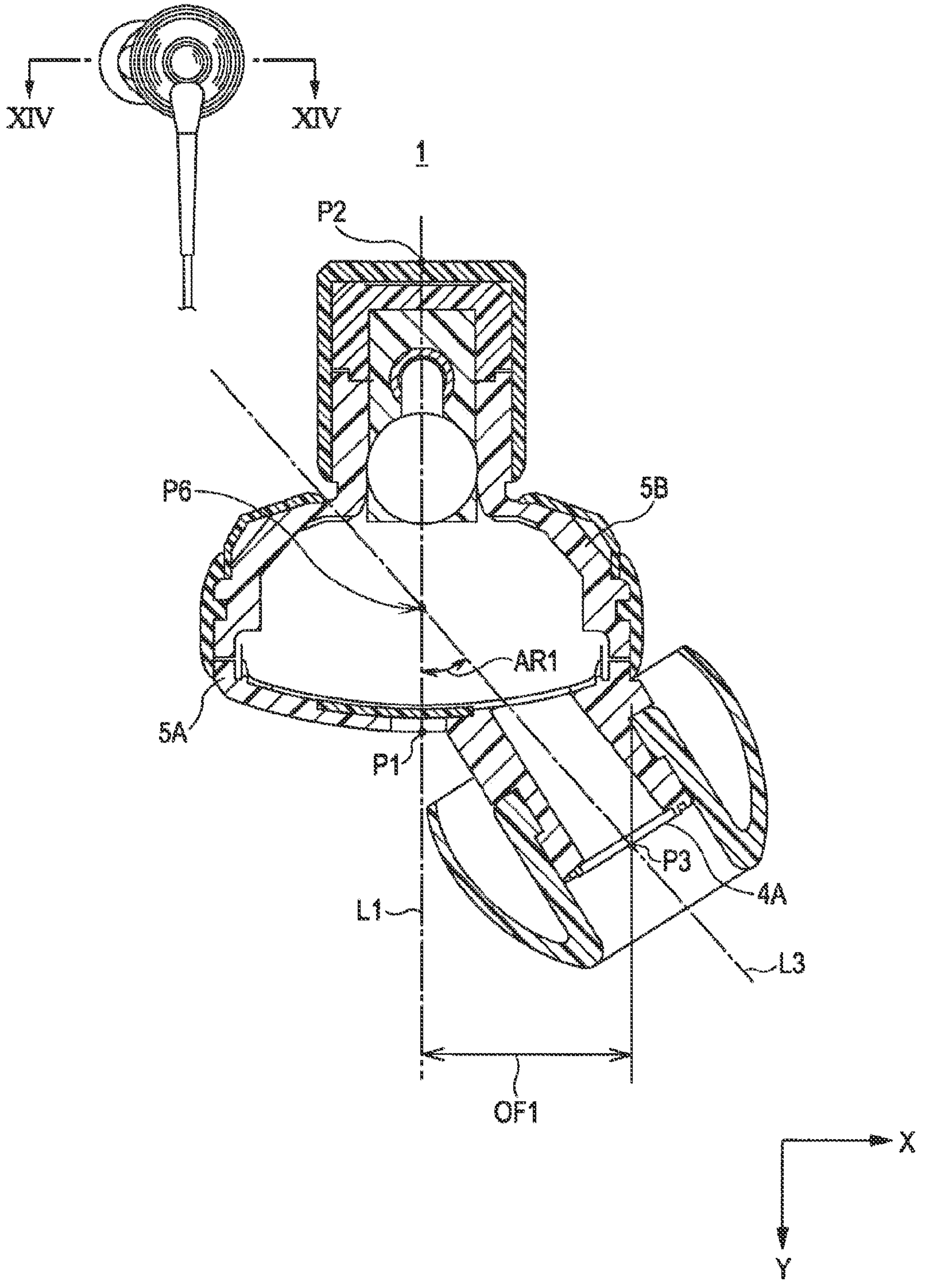
FIG. 14 is a schematic illustration used for description of offset and tilt of a sound guide tube according to another embodiment.

While the tilt angle AR1 is an angle about the intersection point. P5 defined by the center axis line L2 of the sound guide tube 4 and the center line L1 of the housing 5 in the above-described embodiment, the present invention is not limited thereto. For example, as shown in FIG. 14 which is the cross section viewed from the top showing the earphone device 1 taken along the line XIV-XIV, the tilt angle AR1 may be an angle about an intersection point P6 defined by a line L3 passing through the sound guide tube tip midpoint P3 and the center line L1 of the housing 5.

While the offset amount OF1 is a distance extending in the X-axis direction from the center line L1 to the sound guide tube base point P4 in the above-described embodiment, the present invention is not limited thereto. For example, as shown in FIG. 14 which is the cross section viewed from the top showing the earphone device 1 taken along the line XIV-XIV, the offset amount OF1 may be any distance extending in the X-axis direction from the center line L1 to one of characteristic points present within the sound guide tube 4, such as a distance extending in the X-axis direction from the center line L1 to the sound guide tube tip midpoint P3.

The earpiece 3 may vary in size to be detachably attached to the sound guide tube 4. In particular, the outside diameter t3 of the earpiece 3 may include sizes 10, 12, and 14 mm, to allow the user who wears it may select the earpiece 3 in accordance with the size of the user's external auditory meatus (earhole), thereby further improving the fitting comfortability. While the earphone device 1 as an exemplary earphone device is configured by the housing 5 as an exemplary housing and the sound guide tube 4 as an exemplary sound guide tube, the present invention is not limited thereto. An earphone device may be configured by one of various types of housings and one of various types of sound guide tubes.

It should be understood by those skilled in the art that various modifications, combinations, sub-combinations and alterations may occur depending on design requirements and other factors insofar as they are within the scope of the appended claims or the equivalents thereof.

What is claimed is:

1. An earphone comprising;

a housing which houses a driver unit, wherein the housing includes a housing front portion and a housing rear portion, wherein the housing front portion and the housing rear portion are mechanically fused together, and the housing front portion and the housing rear portion are part of the primary enclosure for the driver unit;

a sound guide tube mounted on the housing front portion to protrude from a front surface of the housing, wherein the sound guide tube is at a position deviated from a middle axis line which runs through a middle of both the housing front portion and the housing rear portion, the sound guide tube being integrated to the housing front portion; and a cord knot of a cord located within the housing.

2. The earphone according to claim 1, further comprising:

a cord retainer integrated with the housing, wherein the cord knot is located near one end of the cord retainer.

3. The earphone according to claim 1, wherein:

the cord knot is located behind the driver unit.

4. The earphone according to claim 3, wherein:

the cord knot is located behind the driver unit on the middle axis line of the driver unit.

5. The earphone according to claim 1, wherein:

the cord knot is located behind a base portion of the sound guide tube.

6. The earphone according to claim 1, wherein:

the sound guide tube, including a tip portion and a base portion, deviates from the middle axis line of the driver unit, and the cord knot is located closer to the base portion than the tip portion.

7. The earphone according to claim 1, wherein:

the sound guide tube, including a tip portion and a base portion, is tilted away from and relative to the middle axis line of the driver unit by a predetermined angle, and the cord knot is located closer to the base portion than the tip portion.

8. The earphone according to claim 1, wherein:

the cord knot is located at the housing rear portion.

9. The earphone according to claim 1, wherein:

a drawn direction in which the cord is drawn from the housing is approximately orthogonal to both the middle axis line of the driver unit and a center axis line of the sound guide tube.

10. The earphone according to claim 1, wherein:

a drawn direction of the cord being drawn from the housing is totally orthogonal to both the center line of the driver unit and the center axis line of the sound guide tube.

11. The earphone according to claim 1, wherein:

a drawn direction in which the cord being drawn from the housing is orthogonal to a theoretical surface defined as including the middle axis line of the driver unit and a center axis line of the sound guide tube.

12. The earphone according to claim 1, further comprising:

a cord retainer integrated with the housing, wherein the cord retainer is configured to allow a user to pinch the cord retainer with fingertips when the user is wearing the earphone.

13. The earphone according to claim 1, wherein:

an intersection point of the middle axis line of the driver and the center axis line of the sound guide tube is located near the center of the cord knot.

14. The earphone according to claim 1, wherein:

an intersection point of the middle axis line of the driver unit and the center axis line of the sound guide tube is located within the cord knot.

15. The earphone according to claim 1, wherein:

the cord knot is on the middle axis line of the driver unit.

16. The earphone according to claim 1, further comprising:

a hole on the front surface, wherein the hole and the cord knot are on the middle axis line of the driver unit.

17. The earphone according to claim 1, further comprising:

a cord retainer integrated with the housing, configured such that a part of the cord retainer is located outside of a cavum conchae of a user, when the user is wearing the earphone.

18. The earphone according to claim 1, further comprising:

a cord retainer, shaped substantially cylindrical and integrated with the housing.

19. The earphone according to claim 1, wherein:

the housing front portion comprises the front surface of the housing;

directly behind the front surface is a porous protection plate;

directly behind the porous protection plate is the driver unit comprising a voice coil; and a line of sight exists, looking through the sound guide tube between a tip of the sound guide tube and a portion of the voice coil.

20. The earphone of claim 19, wherein:

the line of sight between the tip of the sound guide tube and the portion of the voice coil goes through the porous protection plate.

* * * * *